(12) United States Patent
Ota

(10) Patent No.: US 11,885,754 B2
(45) Date of Patent: Jan. 30, 2024

(54) TOLERANCE ERROR ESTIMATING APPARATUS, METHOD, PROGRAM, RECONSTRUCTION APPARATUS AND CONTROL APPARATUS

(71) Applicant: Rigaku Corporation, Tokyo (JP)

(72) Inventor: Takumi Ota, Tokyo (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 17/703,041

(22) Filed: Mar. 24, 2022

(65) Prior Publication Data

US 2022/0307994 A1 Sep. 29, 2022

(30) Foreign Application Priority Data

Mar. 26, 2021 (JP) .................. 2021-053075

(51) Int. Cl.
*G06T 11/00* (2006.01)
*G01N 23/046* (2018.01)
*G01N 23/083* (2018.01)

(52) U.S. Cl.
CPC ......... *G01N 23/046* (2013.01); *G01N 23/083* (2013.01); *G06T 11/005* (2013.01);
(Continued)

(58) Field of Classification Search
CPC ............... G01N 23/046; G01N 23/083; G01N 2223/04; G01N 2223/3303;
(Continued)

(56) References Cited

U.S. PATENT DOCUMENTS 7,570,734 B2 8/2009 Arai et al.
9,042,510 B2 5/2015 Voland et al.
(Continued)

FOREIGN PATENT DOCUMENTS

DE 10 2004 035841 A1 3/2005
DE 10 2012 203086 A1 8/2013
(Continued)

OTHER PUBLICATIONS

Translation of WO2013004788 (Year: 2013).*
(Continued)

*Primary Examiner* — David P Porta
*Assistant Examiner* — Mamadou Faye
(74) *Attorney, Agent, or Firm* — ASLAN LAW, P.C.

(57) ABSTRACT

A tolerance error estimating apparatus, method, program, reconstruction apparatus and control apparatus capable of estimating a deviation of a drive axis from a reference position with respect to driving time are provided. A tolerance error estimating apparatus (processing apparatus 300) X-ray analysis apparatus comprises a specific position calculating section 320 for obtaining a specific position of a reference sample at each rotation driving time from X-ray detection images and a deviation amount calculating section 330 for calculating the deviation amount $\Delta x$ in the x direction and $\Delta y$ in the y direction of the center position of a rotation drive shaft as the rotation drive axis at each rotation driving time from the reference position based on the specific position, when the z direction of the orthogonal coordinate system fixed to the sample is set the direction parallel to the rotation drive axis.

12 Claims, 16 Drawing Sheets

(52) U.S. Cl.
CPC . *G01N 2223/04* (2013.01); *G01N 2223/3303* (2013.01); *G01N 2223/401* (2013.01); *G01N 2223/419* (2013.01)

(58) Field of Classification Search
CPC ....... G01N 2223/401; G01N 2223/419; G01N 2223/3032; G01N 2223/306; G01N 2223/32; G06T 11/005; A61B 6/032; A61B 6/5205; A61B 6/584
See application file for complete search history.

(56) References Cited

U.S. PATENT DOCUMENTS

| | | | |
|---|---|---|---|
| 10,801,972 | B2 | 10/2020 | Wuestenbecker |
| 2005/0047552 | A1 | 3/2005 | Arai et al. |
| 2013/0235970 | A1 | 9/2013 | Voland et al. |
| 2014/0200708 | A1* | 7/2014 | Rollet ..................... B23H 7/18 700/162 |
| 2019/0277779 | A1 | 9/2019 | Wuestenbecker |
| 2021/0109039 | A1* | 4/2021 | Rothe ..................... G06T 15/08 |
| 2022/0260505 | A1* | 8/2022 | Rizzello ............... G01N 33/445 |

FOREIGN PATENT DOCUMENTS

| | | |
|---|---|---|
| JP | 3964155 B2 | 8/2007 |
| JP | 2010-193965 A | 9/2010 |
| JP | 2018-099175 A | 6/2018 |
| WO | WO 2013/004788 A1 | 1/2013 |
| WO | WO-2013004788 A1 * | 1/2013 ............. A61B 6/035 |

OTHER PUBLICATIONS

European Patent Office, EP Search Report issued in EP Application No. 22 164 256.4, Munich Germany, dated Aug. 2, 2022, 10 pages.
EP Office Action issued in EP patent application No. 22 164 256.4, European Patent Office (EPO), Germany, dated Oct. 17, 2023, 8 pages.

* cited by examiner

| t | $\theta$ | $u_0$ | $v_0(\Delta z)$ | $\Delta x$ | $\Delta y$ | SODa |
|---|---|---|---|---|---|---|
| $t_1$ | $\theta_1$ | $u_{01}$ | $v_{01}(\Delta z_1)$ | $\Delta x_1$ | $\Delta y_1$ | $SODa_1$ |
| $t_2$ | $\theta_2$ | $u_{02}$ | $v_{02}(\Delta z_2)$ | $\Delta x_2$ | $\Delta y_2$ | $SODa_2$ |
| $t_3$ | $\theta_3$ | $u_{03}$ | $v_{03}(\Delta z_3)$ | $\Delta x_3$ | $\Delta y_3$ | $SODa_3$ |
| ... | ... | ... | ... | ... | ... | ... |

FIG. 8

TOLERANCE ERROR ESTIMATING APPARATUS, METHOD, PROGRAM, RECONSTRUCTION APPARATUS AND CONTROL APPARATUS

CROSS-REFERENCE TO RELATED APPLICATIONS

This application claims priority to JP Patent Application No. 2021-053075 filed on Mar. 26, 2021, the entire contents of which are hereby incorporated by reference.

RELATED ART

Field of the Invention

The present invention relates to a tolerance error estimating apparatus for estimating a tolerance error of a rotation drive axis in an X-ray analysis apparatus, a method, a program, a reconstruction apparatus and a control apparatus.

Description of the Related Art

In the X-ray CT apparatus, the gantry rotation axis or the sample rotation axis (hereinafter referred to as "CT rotation axis") deviates during measurement, thereby causing image degradation. This deviation is called tolerance error, and conventionally correction thereof has been attempted by various methods.

For example, a method of correcting the tolerance error by aligning images is known (See Patent Document 1). In this method, the positional deviation confirmed by superimposing and outputting a two-dimensional projection image and a three-dimensional reconstructed image is corrected. As a result, it is possible to correct the center shift and the SOD (Source-to-Object Distance). In this case, it is possible to increase the accuracy by repeatedly reconstructing the image and using the alignment of the projection image and the projection image of the reconstructed image.

A method of correcting a tolerance error using a sensor is also known (see Patent Document 2). By this method, the deviation in the radial and thrust directions can be corrected using distance sensors.

Patent Documents

Patent Document 1: Japanese Unexamined Patent Application Publication No. 2010-193965
Patent Document 2: Japanese Unexamined Patent Application Publication No. 2018-99175

However, when a tolerance error is corrected by alignment of images, a reconstructed image is required, and it takes time to process the reconstruction. Further, in the case of using a sensor, although it does not take a long time for checking the error, the manufacturing cost is increased according to measurement accuracy required for the sensor itself and a way the sensor is installed.

SUMMARY OF THE INVENTION

The present invention has been made in view of such circumstances, and an object thereof is to provide a tolerance error estimating apparatus, a method, a program, a reconstruction apparatus and a control apparatus capable of estimating a deviation from a reference position of a drive axis with respect to driving time.

(1) In order to achieve the above object, a tolerance error estimating apparatus of the present invention is a tolerance error estimating apparatus for estimating a tolerance error of a rotation drive axis of an X-ray analysis apparatus, and comprises a specific position calculating section for obtaining a specific position of a reference sample at each rotation driving time from an X-ray detection images; and a deviation amount calculating section for calculating a deviation amount $\Delta x$ in the x direction and $\Delta y$ in the y direction of the center position of a rotation drive shaft as the rotation drive axis at each rotation driving time from the reference position based on the specific position, when the z direction of an orthogonal coordinate system fixed to the sample is set to a direction parallel to the rotation drive axis. Thus, by calculating the deviation from the reference position of the drive axis with respect to the driving time using the X-ray detection images, it is possible to obtain high-quality data at low cost and at high speed.

(2) Further, in the tolerance error estimating apparatus of the present invention, the deviation amount calculating section assumes the respective functional forms of $\Delta x$ and $\Delta y$ for each rotation driving time, determines the function $\Delta x(t)$ used for the calculation of $\Delta x$ and the function $\Delta y(t)$ used for the calculation of $\Delta y$ by optimizing parameters of the assumed functional forms, and uses the determined $\Delta x(t)$ and $\Delta y(t)$ to calculate the $\Delta x$ and $\Delta y$ at each rotation driving time. Thus, $\Delta x$ and $\Delta y$ varied by the rotation angle can be estimated with high accuracy.

(3) Further, in the tolerance error estimating apparatus of the present invention, the deviation amount calculating section optimizes the parameters of the assumed functional forms so as to minimize an evaluation function representing a degree of coincidence between the specific position obtained from the X-ray detection images and the specific position calculated using the respective functional forms of the assumed $\Delta x$ and $\Delta y$. Thus, $\Delta x$ and $\Delta y$ can be easily estimated with high accuracy using the X-ray detection images.

(4) Further, in the tolerance error estimating apparatus of the present invention, the deviation amount calculating section calculates the $\Delta x$ and $\Delta y$ by assuming that the respective functional forms of $\Delta x$ and $\Delta y$ are periodic functions each having a period of rotation drive. Thus, by taking advantage of the fact that $\Delta x$ and $\Delta y$ return to the same numerical value in one rotation and assuming that they are periodic functions, $\Delta x$ and $\Delta y$ can be easily estimated.

(5) Further, in the tolerance error estimating apparatus of the present invention, the X-ray detection image is acquired by a two-dimensional detector having a detecting element with 50 μm or less width. Thus, the apparatus is particularly applicable to inspection of industrial products for which CT images of micron accuracy are required.

(6) Further, the tolerance error estimating apparatus of the present invention further comprises a table storing section for storing a table including parameters for correction based on the calculated $\Delta x$ and $\Delta y$. Thus, it is unnecessary to recalculate the specific position or calculate the corrected SOD at the time of data correction or drive control correction.

(7) Further, the tolerance error estimating apparatus of the present invention further comprises a display processing section for displaying $\Delta x$ and $\Delta y$ over one rotation calculated by the deviation amount calculating section as a trajectory of a tolerance error. Thus, the user can recognize the state of the X-ray analysis apparatus at the time of acquiring the data used for calculating the deviation amount from the shape of the displayed trajectory.

(8) Further, the tolerance error estimating apparatus of the present invention further comprises a designation accepting section for accepting designation of the means for applying Δx and Δy and activates a reconstruction function or a control function according to the accepted designation. Thus, the user can choose whether to correct the tolerance error on software or hardware.

(9) Further, in a reconstruction apparatus of the present invention, the X-ray analysis apparatus is an X-ray CT apparatus, and the reconstruction apparatus comprises a reconstruction section for performing reconstruction of a three-dimensional image using the CT projection images obtained by correcting a deviation amount calculated by the tolerance error estimating apparatus described in any one of (1) to (8) above. Thus, it is possible to generate a reconstructed image corrected using the projection images including the tolerance error without being required particularly adjustment of the optical system, etc.

(10) Further, a control apparatus of the present invention comprises a correction controlling section for controlling correction of the X-ray analysis apparatus based on the deviation amount calculated by the tolerance error estimating apparatus described in any one of (1) to (8) above. Thus, since it is possible to acquire images while adjusting the relative position of the sample at the time of measurement, it is possible to perform highly accurate measurement using the X-ray detection image obtained.

(11) Further, a method of the present invention is a method of estimating a tolerance error of a rotation drive axis of an X-ray analysis apparatus, which comprises steps of obtaining a specific position of a reference sample at each rotation driving time from X-ray detection images, and calculating the deviation amount Δx in the x direction and Δy in the y direction of the center position of a rotation drive shaft as the rotation drive axis at each rotation driving time from the reference position based on the specific position, when the z direction of an orthogonal coordinate system fixed to a sample is set the direction parallel to the rotation drive axis. Thus, high-quality data can be obtained at low cost and at high speed.

(12) Further, a program of the present invention is a program for estimating a tolerance error of a rotation drive axis of an X-ray analysis apparatus, which makes a computer execute processes of obtaining a specific position of a reference sample at each rotation driving time from X-ray detection images, and calculating the deviation amount Δx in the x direction and Δy in the y direction of the center position of a rotation drive shaft as the rotation drive axis at each rotation driving time from the reference position based on the specific position, when the z direction of an orthogonal coordinate system fixed to a sample is set the direction parallel to the rotation drive axis. Thus, high-quality data can be obtained at low cost and at high speed.

According to the present invention, by estimating the deviation of the rotation drive axis from the reference position with respect to the driving time, it is possible to reduce the burden on correction of the tolerance error.

BRIEF DESCRIPTION OF THE DRAWINGS

FIG. 8 is a diagram showing an image of a table.

DETAILED DESCRIPTION OF THE INVENTION

Figure 1:
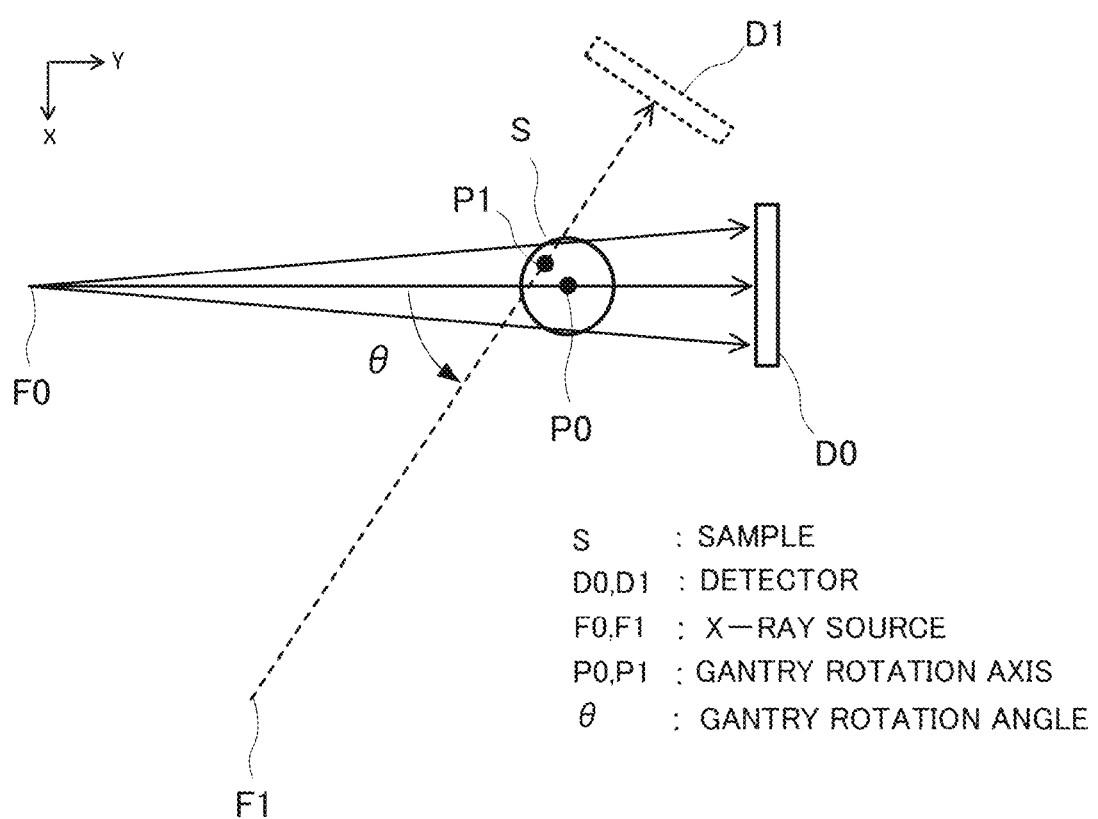
FIG. 1 is a schematic diagram showing a configuration of an X-ray CT apparatus in which tolerance error has occurred.

Next, embodiments of the present invention are described with reference to the drawings. To facilitate understanding of the description, the same reference numerals are assigned to the same components in the respective drawings, and duplicate descriptions are omitted.

[Principle]

An X-ray CT apparatus irradiates a sample with a cone-shaped or parallel beam of X-rays from all angles and acquires a distribution of the absorption coefficient of the X-rays, that is, a projection image, by a detector. To irradiate X-rays from any angle, the X-ray CT apparatus is configured to rotate a sample stage with respect to the fixed X-ray source and the detector or to rotate the gantry integrated with the X-ray source and the detector. The rotation is relative, and a rotation angle refers to an angle that occurs between the gantry and the sample and is also referred to as a projection angle. Incidentally, the rotation angle is basically proportional to rotation driving time.

The X-ray CT apparatus is a type of X-ray analysis apparatus, comprises a CT rotation axis as a rotation driving axis, and acquires X-ray CT projection images as X-ray detection images. When estimating the tolerance error of the X-ray CT apparatus, a reference sample used for acquiring the X-ray detection images is a sphere of uniform density, a specific position used for calculating the amount of deviation is a centroid position of the absorption coefficient.

Thus, the projection is performed from various angles, and the distribution of the linear absorption coefficient of the sample can be estimated by shading of the obtained projection image of the sample. Then, it is called reconstruction that a three-dimensional line absorption coefficient distribution is obtained from two-dimensional projection images. Basically, back-projection of the projection images is performed.

In the X-ray CT apparatus as described above, the adjustment is performed so that the CT rotation axis is positioned at the reference position of the sample placed on the straight line connecting the center of the radiation source and the detector. If the CT rotation axis is rotated during measurement, the CT rotation axis may deviate from the reference position of the sample (tolerance error). FIG. 1 is a schematic diagram showing a configuration of an X-ray CT apparatus in which tolerance error has occurred. When the CT rotation axis is rotated by a rotation angle θ (gantry rotation angle), the X-ray source F0 and the detector D0 attached to the gantry move to the position of F1 and D1. At the time, the CT rotation axis (gantry rotation axis) coincides with the reference position of the sample at first at the position P0, but the position of the CT rotation axis deviates from P0 to P1 with the rotation of the CT rotation axis. This deviation is the tolerance error.

Figure 2A:
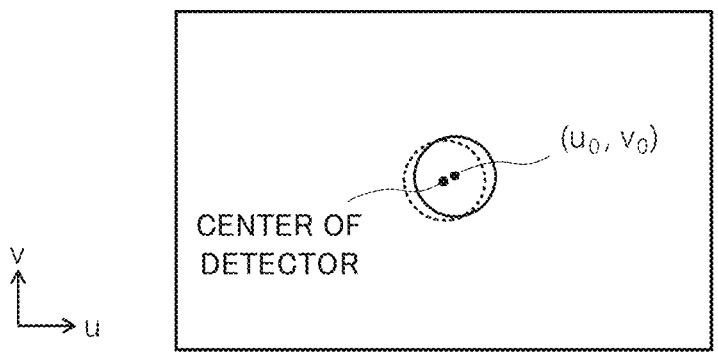
FIGS. 2A and 2B are schematic diagrams of projection images obtained when each tolerance error has occurred.
Figure 2B:
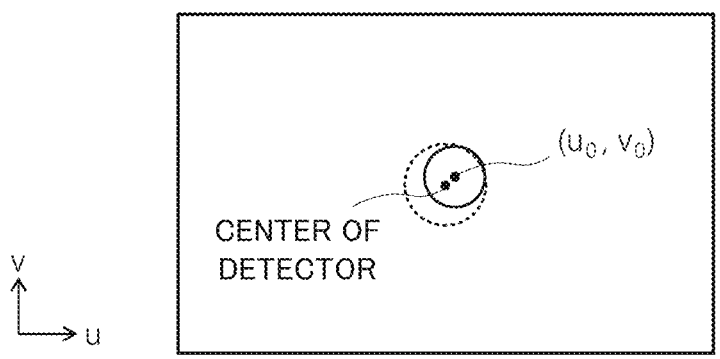

FIGS. 2A and 2B are schematic diagrams of projection images obtained when each tolerance error has occurred. A rectangular frame indicates the region of the entire projection image detected by the detection plane. In the projection image, a direction parallel to the CT rotation axis is defined as v, and a direction orthogonal to v is defined as u. The external shape and centroid (u0, v0) of the projection image of the sample are shown when a sphere of uniform density is used as a reference sample. The projection image when the CT rotation axis is adjusted to be positioned at the reference position of the sample is shown by a broken line.

Figure 3:
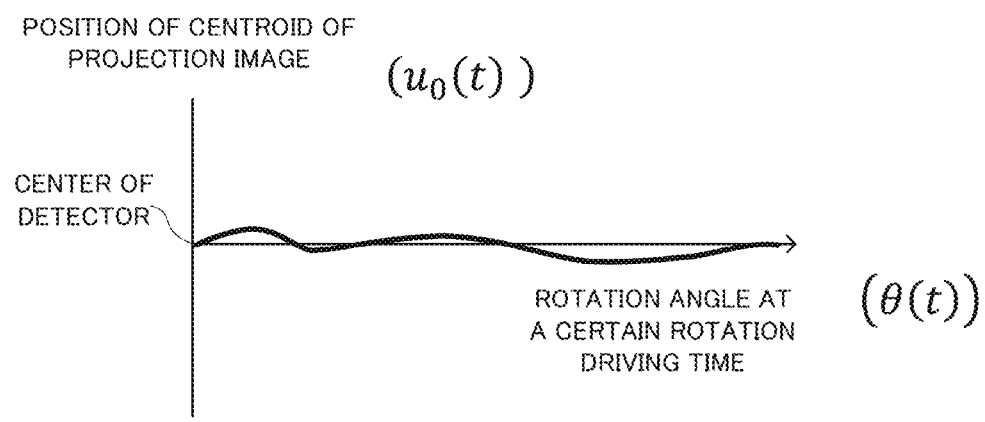
FIG. 3 is a graph showing the variation of the centroid position of the projection image in the u direction due to the tolerance error.

FIG. 3 is a graph showing the variation of the centroid position of the projection image in the u direction due to the tolerance error. The position of the centroid of the projection image moves with respect to the center position of the detector, and the direction and amount of movement varies with respect to the rotation driving time (t). Deviation in the direction parallel to the detector plane (u direction) and the deviation with respect to the SOD direction occurring in the CT rotation axis affect the projection image differently.

If the CT rotation axis deviates parallel to the detection surface (FIG. 2A), the outer shape of the projection image does not change, only the centroid position moves on the detector plane. In the case that there is also a deviation in the SOD direction (FIG. 2B), even if the movement amount of the centroid position is the same, since the magnification ratio varies when a deviation occurs in the SOD direction, the size of the outer shape of the projection image also changes accordingly. Therefore, when the amount of movement of the centroid position of the projection image is corrected as a tolerance error, since the deviation of the SOD direction remains, even if the reconstruction is performed using such a projection image there remains a blur due to the tolerance error in the reconstructed image. Therefore, when correcting the tolerance error, it is necessary to consider which direction and how much the CT rotation axis moves with respect to the rotation driving time.

In the present invention, when the position where the sample is installed is treated as a reference position, it is a feature to represent how much the center position of a CT rotation shaft deviates as the rotation drive axis from the reference position by a function of the rotation driving time (t). By determining the optimal parameters of the assumed functions, the amount of deviation (Δx, Δy, Δz) of the center position of the CT rotation shaft from the reference position at each rotation driving time can be estimated.

When optimizing the parameters of the function, CT measurement is performed with a sphere of uniform density as a reference sample, and the position of the centroid of the absorption coefficient is used in the projection image of the sphere projected on the acquired CT projection image. The sphere of uniform density is preferably a metal sphere, but more preferably a steel sphere. When the amount of deviation with respect to the driving time is reproducible, the amount of deviation with respect to the driving time can be reflected in the tolerance error correction of the experimental measurement by estimating the amount of deviation with respect to the driving time from reliable data. And, the centroid position can simply be calculated, if the contrast of the projection image is clear like a steel ball, and if a sample has isotropic shape.

Figure 4A:
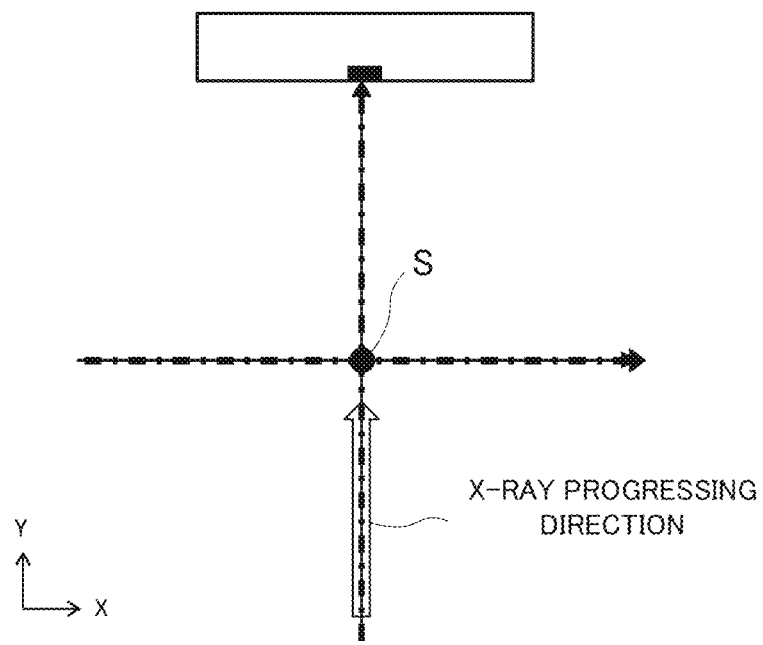
FIGS. 4A and 4B are projected views in the z direction showing the respective coordinate systems before and after the error occurs, respectively.
Figure 4B:
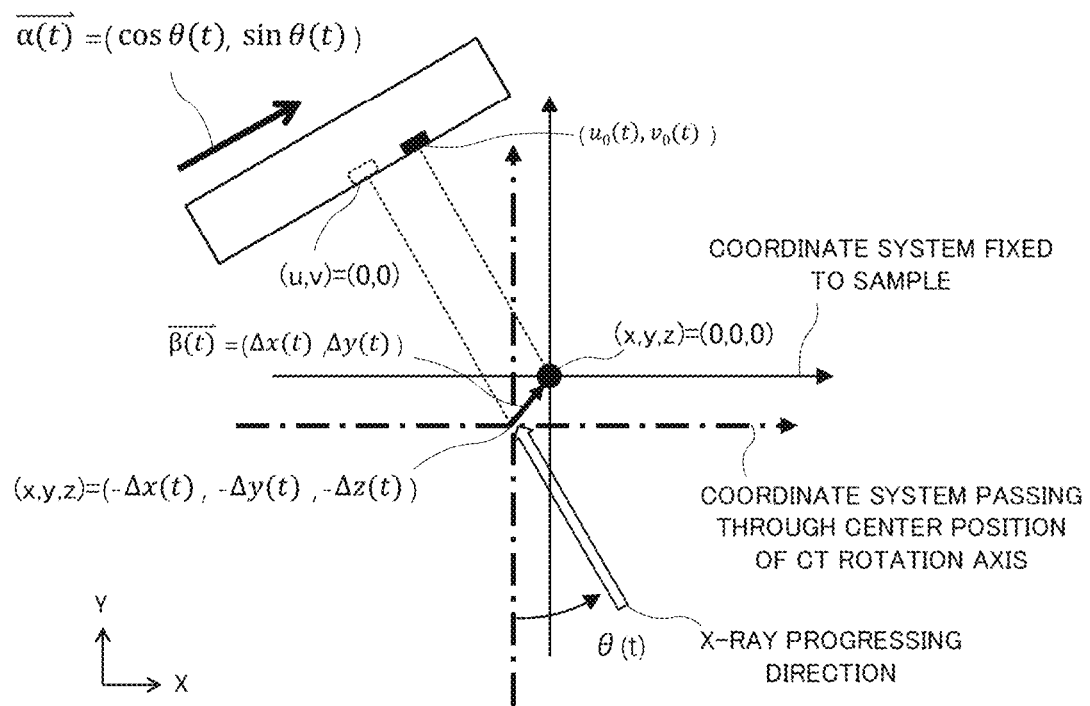

FIGS. 4A and 4B are projected views in the z direction showing the respective coordinate systems before and after the error occurs, respectively. FIGS. 4A and 4B show the principles of estimating a deviation quantity in the X-ray CT apparatus. The reference coordinates are set at the position where the sample is placed, and the origin position is (0, 0, 0). When the coordinates with the center position of the CT rotation shaft as the origin are set, the reference position of the sample coincides with the center position of the CT rotation shaft at the initial time of the rotation drive. The center position of the detector also coincides with the centroid of the projection image on the projection image.

At the time of CT measurement, the center position of the CT rotation shaft (origin of the coordinates) is deviated by ($-\Delta x$ (t), $-\Delta y$ (t), $-\Delta z$) in the arrangement of the rotation angle (θ(t)) at a certain rotation driving time of the CT rotation axis. At this time, the deviation of the center position of the CT rotation shaft is represented by a vector $\vec{\beta}(t)$. Further, when the unit vector in the u direction parallel to the detection plane is represented as the relation (1), u0(t) is as shown in the relation (2).

$$\vec{\alpha(t)} : \text{the unit vector in the } u \text{ direction parallel to the detection plane} \quad (1)$$

$$u_0(t): \text{the orthographic projection of } \vec{\beta(t)} \text{ onto the detection plane} \quad (2)$$

The length v0(t) in the v direction parallel to the detection plane coincides with the deviation in the z direction of the center position of the CT rotation shaft. These relationships are expressed by the following equations (Helgason-Ludwig condition).

$$u_0(t) = \vec{\alpha(t)} \cdot \vec{\beta(t)} = \Delta x(t)\cos\theta(t) + \Delta y(t)\sin\theta(t) \quad (3)$$

$$v_0(t) = \Delta z(t) \quad (4)$$

(1) Assuming Functional Forms of Δx(t) and Δy(t)

The factors of tolerance error differ depending on the assembly and material of the drive axis, etc. Therefore, the function is specified from the tendency of the direction and the amount of deviation. For example, when the deviation direction and the amount are constant in such cases that the member of the drive axis expands or contracts by an environment such as temperature or is affected by the stress applied in one direction, a simple functional form such as a linear function can be used. In the case of an X-ray CT apparatus, since it is expected that a certain amount or the same amount of deviation is repeated in a certain range around the axis of the CT rotation axis for each period of rotation, it is preferable to assume a periodic function.

When deviation Δx (t) and Δy (t) in a certain rotation driving time (t) are the periodic functions of the rotation angle ($\theta(t)$) of a certain rotation driving time, they are expressed by the following equations by the Fourier series expansion.

$$\Delta x(t) = \sum_{i=0}^{i_{max}} a_i^x \cos i\theta(t) + \sum_{j=1}^{j_{max}} b_j^x \sin j\theta(t) \quad (5)$$

$$\Delta y(t) = \sum_{i=0}^{i_{max}} a_i^y \cos i\theta(t) + \sum_{j=1}^{j_{max}} b_j^y \sin j\theta(t) \quad (6)$$

By defining the parameters $\{a_i\}$ and $\{b_j\}$ with respect to the values of $\Delta x$ and $\Delta y$, it is possible to reproduce the variation in the amount of deviation over time in two directions that are perpendicular to each other. In addition, for larger parameters imax and jmax, the functions can contain higher order terms.

(2) Using the Evaluation Function to Optimize the Parameters of the Assumed Function Forms The parameters $\{a_i\}$ and $\{b_j\}$ of the function forms assumed above are optimized in order to calculate the $\Delta x$ and $\Delta y$ in each rotation driving time. The parameters $\{a_i\}$ and $\{b_j\}$ of the assumed functional form are optional constants, and these parameters are optimized so that the specific position of the X-ray detected image coincides with the specific position computed using the function representing $\Delta x(t)$ and $\Delta y(t)$. As an optimization index, an evaluation function representing the degree of coincidence of each specific position is preferably defined.

For example, in estimating the tolerance error of the X-ray CT apparatus, in the rotation driving time (tk) corresponding to the kth projection image, it is preferable to optimize the parameter $\{a_i, b_j\}$ so as to satisfy Helgason-Ludwig condition. Once the parameters are optimized, when the left side of the equation (3) is defined as the position of the centroid of the absorption coefficient of the CT projection image of the reference sample, the difference from the right side is minimized.

The sum of the residual squares of left-side and right-side for all projections (k) is used as the evaluation function. The evaluation function is expressed by the following equation. The parameters $\{a_i, b_j\}$ are determined so as to minimize the evaluation function by the gradient method.

$$F(\{a_i, b_j\}) = \sum_k (u_0(t_k) - \Delta x(t_k)\cos\theta(t_k) - \Delta y(t_k)\sin\theta(t_k))^2 \quad (7)$$

(3) Creating a table to store the deviation amount together with the related information and correcting with referring to the stored value The optimized parameters $\{a_i, b_j\}$ are substituted into $\Delta x(t)$ (formula (5)) and $\Delta y(t)$ (formula (6)) to determine the functions $\Delta x(t)$, $\Delta y(t)$, and SODa(t) for calculating $\Delta x$, $\Delta y$ and SODa. Thus, $\Delta x$, $\Delta y$ and SODa are able to be calculated for each rotation driving time t.

Further, the calculated values used for correction are preferable to be stored in a single table as t, $\theta$ (t), $\Delta x$ (t), $\Delta y$ (t), u0(t), v0(t), and SODa(t). In this case, the storage is performed for each combination of t and $\theta$(t). Thus, the correction amount to be used can be selected in accordance with the correction method.

By storing them as deviation amounts with respect to the rotation driving time t and the rotation angle $\theta$, for example, the correction can be performed with incorporating the variation of the tolerance error when the scan time is varied. u0(t), v0(t) and SODa(t) are stored together with them.

Thus, since the position of the centroid of the absorption coefficient of the projection image of the reference sample used for the estimation of the deviation amount is stored, the values are possible to be directly referred at the time of correction of the reconstruction. As a result, it is possible for the reconstruction apparatus or the control apparatus to recalculate the position of the centroid of the absorption coefficient of the projection image of the reference sample or to eliminate the need to calculate the corrected SOD, i.e., SODa. In addition, the values are preferable to be stored as the inspection result at the time of the inspection of the device such as the shipping inspection and the maintenance of the device, or the periodic inspection result such as once a month, for example. From the stored data table, $\Delta x$ and $\Delta y$ over one rotation during CT measurement may be plotted to output a graph showing the trajectory.

The trajectory represents how much the rotation drive axis has moved in the x and y directions while the rotation drive axis rotates once with reference to the state where the reference position of the sample coincides with the center position of the CT rotation shaft of the sample. From the shape of the trajectory, the state of the X-ray analysis apparatus can be recognized at the time when the data used for the deviation amount calculation is obtained. Since the shape change of the trajectory is stored as device management information, for example, it is possible to determine whether there is deterioration or abnormality of the components related to the rotational drive such as wear of the bearing.

Since the estimated amount of deviation coincides with the amount of movement of the CT rotation axis in the control of the CT rotation axis of the measurement, the amount of deviation can be corrected by performing the movement control so as to cancel the deviation as the correction amount. Since data can be acquired while the amount of deviation being corrected at the time of measurement, correction in data processing is not necessary.

In addition, when the acquired data has an effect of the tolerance error, the data can be corrected by converting the amount of deviation into a correction amount. The coordinates are reset so that the center position of the detector prior to correction is moved by u0(t) and v0(t). The transformation can be performed by the following formula:

$$u'(t) = u(t) - u_0(t) \quad (8)$$

$$v'(t) = v(t) - v_0(t) \quad (9)$$

Since the deviation amount includes information of the moving direction and the movement amount of the CT rotation axis, it is possible to also calculate the deviation with respect to the SOD direction. SODa, which is the corrected SOD, can be calculated by the following formula.

$$SODa(t) = SOD(t) + \Delta x(t)\sin\theta(t) - \Delta y(t)\cos\theta(t) \quad (10)$$

By correcting the data referring to these values during reconstruction, it is possible to reduce the blur of the reconstructed image which is caused by the deviation with respect to the deviation of the CT rotation axis in the direction parallel to the detector plane (u direction, v direction) and the SOD direction.

[Whole System]

Figure 5:
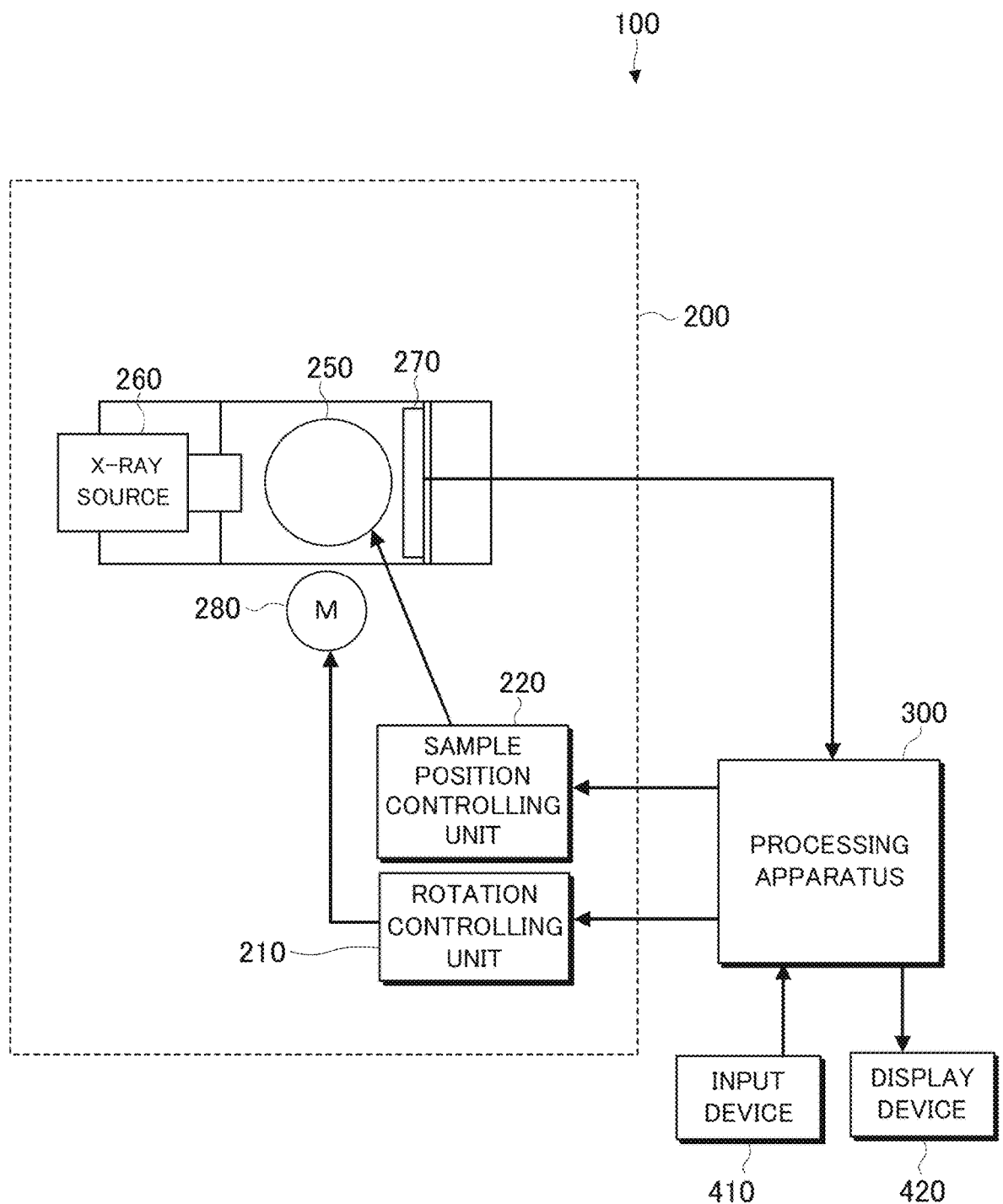
FIG. 5 is a schematic diagram showing a configuration of a whole system.

FIG. 5 is a schematic diagram showing a configuration of a whole system 100 including an X-ray CT apparatus 200, a processing apparatus 300, an input device 410 and a display device 420. Here, the X-ray CT apparatus 200 shown in FIG. 5 is configured to rotate the gantry in which the X-ray source 260 and the detector 270 are integrated with respect to the sample, however, the X-ray CT apparatus 200 is not limited thereto, and may be configured to rotate the sample.

The processing apparatus 300 (tolerance error estimating apparatus) is connected to the X-ray CT apparatus 200 to perform controlling the X-ray CT apparatus 200 and processing the acquired data. The processing apparatus 300 may be a PC terminal or a server on a cloud. The processing apparatus 300 estimates the tolerance error of the CT rotation axis in the X-ray CT data. The input device 410 is, for example, a keyboard or a mouse, and performs input to the processing apparatus 300. The display device 420 is, for example, a display, and is used for showing a result of processing by the processing apparatus 300 to a user by screen display or the like.

[X-Ray CT Apparatus]

As shown in FIG. 5, the X-ray CT apparatus 200 includes a rotation controlling unit 210, a sample position controlling unit 220, a sample stage 250, an X-ray source 260, and a detector 270. The X-ray source 260 and the detector 270 are installed on a gantry (not shown), and X-ray CT measurement is performed by rotating the gantry with respect to a sample fixed to the sample stage 250. In addition, the sample stage 250 installed between the X-ray source 260 and the detector 270 may be rotated.

The X-ray CT apparatus 200 rotates the gantry at a timing instructed by the processing apparatus 300 and acquires a projection image of the sample. The measurement data is transmitted to the processing apparatus 300. The X-ray CT apparatus 200 is suitable for use on precision industrial products such as semiconductor devices, however, can be applied to a device for animals as well as industrial products.

The X-ray source 260 emits X-rays toward the detector 270. The detector 270 is a two-dimensional detector having a receiving surface for receiving X-rays and possible to measure the intensity distribution of X-rays transmitted through the sample by a number of pixels. The X-ray CT projection image is preferably acquired with a two-dimensional detector having detection elements with 50 μm or less width, e.g. pixels of 50×50 μm or less. For example, when the enlargement ratio is 50 times, the size of one pixel is 1 μm. When an image blur of micron order is caused by the tolerance error, the present invention is effective for an X-ray CT apparatus for industrial products in which analysis is carried out with accuracy of micron order especially, because the error occurs in recognizing the shape and measuring the dimension.

The rotation controlling unit 210 rotates the gantry at a speed set at the time of CT measurement. The sample position controlling unit 220 controls a sample position by adjusting a position of the sample stage 250 during the CT measurement. The sample position controlling unit 220 can adjust the sample position in accordance with $\Delta x$, $\Delta y$, and $\Delta z$ at each rotational position according to an instruction from the processing apparatus 300.

[Processing Apparatus]

Figure 6:
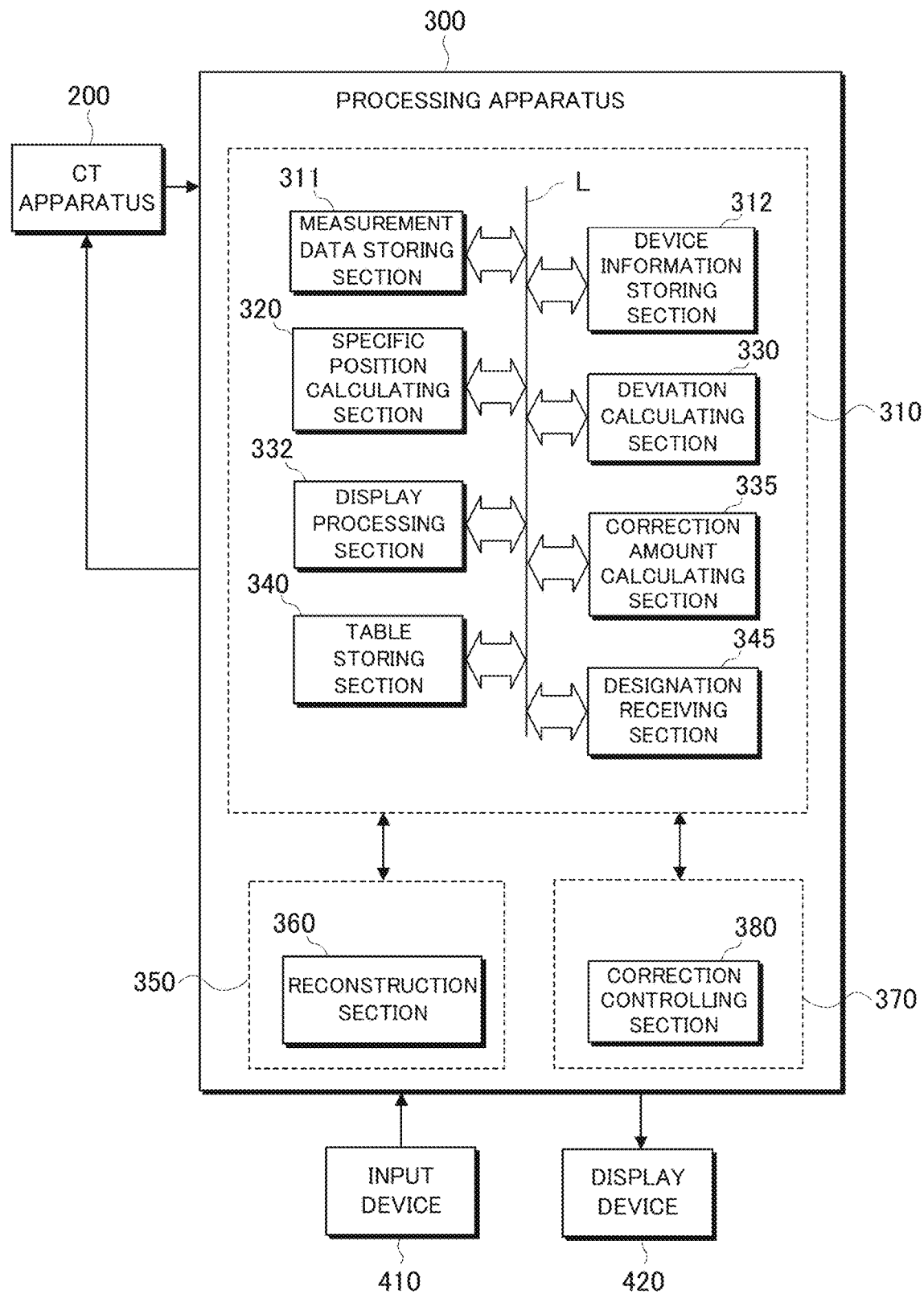
FIG. 6 is a block diagram showing a configuration of the processing apparatus (a tolerance error estimating apparatus, a reconstruction apparatus, and a control apparatus).

FIG. 6 is a block diagram showing a configuration of the processing apparatus 300 (a tolerance error estimating apparatus, a reconstruction apparatus, and a control apparatus). The processing apparatus 300 is configured by a computer formed by connecting a CPU (Central processing section), a ROM (Read Only Memory), a RAM (Random Access Memory) and a memory to a bus. The processing apparatus 300 is connected to the X-ray CT apparatus 200 and receives information. In the example shown in FIG. 6, the processing apparatus 300 functions as each of a tolerance estimation apparatus, a reconstruction apparatus and a control apparatus. However, an independent processing apparatus may be used as each functional apparatus. In any case, the devices are connected to each other so that information can be transmitted and received.

(Tolerance Error Estimating Apparatus)

The processing apparatus 300 includes a measurement data storing section 311, an apparatus information storing section 312, a specific position calculating section 320, a deviation amount calculating section 330, a display processing section 332, a correction amount calculating section 335, a table storing section 340, and a designation receiving section 345. Each section can transmit and receive information via a control bus L. The input device 410 and the display device 420 are connected to the CPU via an appropriate interface.

The measurement data storing section 311 stores measurement data acquired from the X-ray CT apparatus 200. The measurement data includes a rotation driving time (including information corresponding to a rotation driving time such as rotation angle information) and a projection image corresponding thereto. The apparatus information storing section 312 stores apparatus information acquired from the X-ray CT apparatus 200. The apparatus information includes geometry at the time of measurement, etc.

The specific position calculating section 320 obtains the centroid of the absorption coefficient from the X-ray CT projection image of the sphere of uniform density at each rotation driving time. Thus, it is possible to recognize the transition of the center of the sphere with respect to the passing of the rotation driving time in the projection image. The center of the sphere on the projection image represents the projections of the deviation of the center of the CT rotation axis from the reference position of the original sample. However, since $\Delta x$ and $\Delta y$ are not known directly from the projections of the deviation, they are necessary to be estimated.

The deviation amount calculating section 330, based on the centroid position of the u direction, calculates the deviation $\Delta x$ in the x direction and $\Delta y$ in the y direction of the center position of the CT rotation shaft from the reference position of the sample at each rotation driving time when a direction parallel to the CT rotation axis is the z direction of the orthogonal coordinate system fixed to the sample. Thus, by calculating the deviation of the center position of the CT rotation shaft from the reference position of the sample using the projection image without performing reconstruction, it is possible to obtain high-quality data at low cost and at high speed. Details of the calculation of $\Delta x$ and $\Delta y$ are described below.

Specifically, it is preferable to assume respective functional forms of $\Delta x$ and $\Delta y$ with respect to each rotation driving time, to determine the functions $\Delta x(t)$ used for calculating $\Delta x$ and $\Delta y(t)$ used for calculating $\Delta y$ by optimizing the parameters of the assumed functions, and to calculate $\Delta x$ and $\Delta y$ at each rotation driving time using the determined $\Delta x(t)$ and $\Delta y(t)$. Thus, the amount of deviation caused by the tolerance error can be estimated, and the value that can be used for correction can be calculated. The parameters included in the assumed functional forms are preferably optimized so as to minimize the evaluation function representing the degree of coincidence between the specific position of the X-ray detection image and the specific position calculated using $\Delta x$ and $\Delta y$. Thus, it is possible to estimate $\Delta x$ and $\Delta y$ varied by the rotation driving time with high accuracy.

Δx and Δy return to the same value in one cycle of the CT rotation. Using the fact, it is preferable to calculate Δx and Δy by assuming a periodic function having a period of the CT rotation. Thus, Δx and Δy can be easily estimated by assuming the periodic function. The deviation amount calculating section 330 further calculates Δz from the transition of the centroid position in the v direction with respect to the rotation driving time on the projection image.

The display processing section 332 displays Δx and Δy over one rotation calculated by the deviation amount calculating section 330 as a trajectory of tolerance error on the display device 420. As a result, the user can recognize the state of the X-ray analysis apparatus at the time of acquiring the data used for the deviation amount calculation from the shape of the displayed trajectory.

The correction amount calculating section 335 calculates a value necessary for correction using the calculated deviation amounts Δx and Δy. For correction, it is preferable to use a stored table.

The table storing section 340 stores, as a table, the values calculated by the specific position calculating section 320, the deviation amount calculating section 330, and the correction amount calculating section 335. In the table, the specific position, the amount of deviation, and the correction value of the X-ray image are specified for each combination of the rotation driving time and the rotation angle corresponding thereto.

The designation accepting section 345 accepts a screen for designating a means for applying the deviation amounts in the x and y directions. The processing apparatus 300 starts the reconfiguration function or the control function according to the accepted designation. Thus, the user can choose whether to correct the tolerance error on software or hardware.

(Reconstruction Apparatus)

The reconstruction apparatus 350 includes a reconstruction section 360. The reconstruction apparatus 350 causes the reconstruction section 360 to reconstruct a three-dimensional image based on the corrected X-ray CT projection images of the sample. Thus, it is possible to generate a reconstructed image which does not require particularly adjustment of the optical system, etc., and which is corrected using the projection image including the tolerance error. The reconstruction section 360 reconstructs a three-dimensional image based on the X-ray CT projection images.

(Control Apparatus)

The control apparatus 370 includes a correction controlling section 380, and the correction controlling section 380 controls the position of the sample for the correction at the time of CT test using the calculated Δx, Δy, and Δz. For correction, it is preferable to use the stored table. Thus, since it is possible to get the projection images while adjusting the relative position of the sample at the time of measurement, it is possible to generate a highly accurate reconstructed image without correction using the obtained projection images.

[Tolerance Error Estimating Method]

Figure 7:
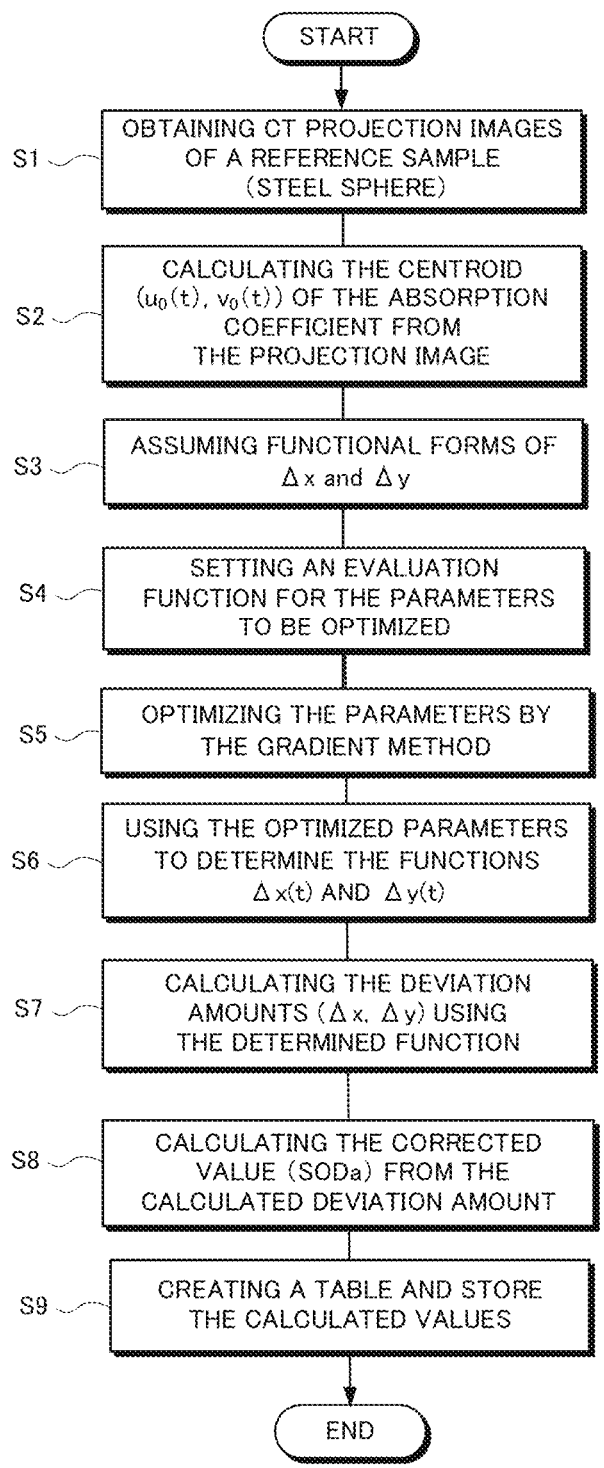
FIG. 7 is a flowchart showing a tolerance error estimating method of the present invention.

A tolerance error estimating method using the whole system 100 configured as described above is described. FIG. 7 is a flowchart showing a tolerance error estimating method. First, in step S1$i$, a CT projection image is acquired using a steel ball as a reference sample which is a sphere of uniform density. Next, the centroid position u0(t) and v0(t) of the absorptivity are calculated from the acquired CT projection image (step S2).

Next, a functional form of the deviation Δx and Δy at the rotation driving time is assumed (step S3). Since the factors of the tolerance error differ depending on the state of the components constituting the device, it is preferable to be able to select a functional form capable of reproducing the transition in the amount of deviation with respect to each rotation driving time. For example, a screen in which a user can select a function form such as a primary function or a periodic function may be displayed.

Next, an evaluation function is set for the parameter to be optimized (step S4). The evaluation function is set based on information on the specific position of the X-ray detection image, the specific position calculated using Δx and Δy, and the number of projections. The parameters are optimized by the gradient method (step S5). At the time, a graph plotted the specific position of the X-ray detection image and the specific position calculated using Δx and Δy with respect to the rotation angle at each rotation driving time or each rotation driving time may be output. Thus, the probability of the optimized parameters can be visually confirmed.

Next, functions Δx(t) and Δy(t) are determined using the optimized parameters (step S6). The deviation amounts (Δx, Δy) are calculated using the determined function (step S7). The corrected values (SODa) are calculated from the calculated deviation amounts (step S8). Then, the specific position of the calculated X-ray image, the deviation amount and the correction values are stored as a table (step S9). Thus, it is possible to estimate the tolerance error.

[Correcting Method]

A reconstructed image can be generated by correcting the tolerance error estimated as described above. The correcting method includes two methods: a method using software and a method controlling an X-ray CT apparatus during measurement. It is preferable that the processing apparatus 300 displays a screen on which the user can select which means is used to perform the correction and whether the correction is applied or not, and the like.

When software is used, a desired sample is first CT measured. The obtained projection images are corrected using the tables of Δx, Δy and Δz. Specifically, the center shift and the SOD are corrected. The three-dimensional image is reconstructed using the corrected projection images. Thus, a reconstructed image whose tolerance error is easily corrected only by processing is obtained.

When the X-ray CT apparatus is controlled at the time of measurement, CT measurement is performed while controlling the sample position for the correction using the tables of Δx, Δy, and Δz at the time of CT measurement of a desired sample. In the projection image thus obtained, a tolerance error has been corrected. The three-dimensional image is reconstructed using the obtained projection image. Thus, a highly accurate reconstructed image with reduced error from the device can be obtained.

In this way, it is preferable that the estimated Δx, Δy and Δz be held as a table. FIG. 8 is a diagram showing an image of a table. As shown in FIG. 8, the rotation angle (θ1, θ2, θ3, ... ), the centroid position of the absorption coefficient in the u direction (u01, u02, u03, ... ), the centroid position of the absorption coefficient in the v direction (v01(Δz1), v02(Δz2), Δ03(Δz3), ... ), the deviation amount in the X direction (Δx1, Δx2, Δx3, ... ), the deviation amount in the Y direction (Δy1, Δy2, Δy3, ... ), and the corrected SOD (SODa1, SODa2, SODa3, ... ) are stored with respect to each driving time (t1, t2, t3, ... ) in each constant step. As each rotation driving time for each constant step, for example, each rotation driving time for acquiring the projection image may be used.

Other Embodiments

Although the above embodiment is directed to the estimation and correction of tolerance error of an X-ray CT apparatus, the present invention can be applied to other X-ray analysis apparatuses. An X-ray diffractometer includes a rotation drive axis for rotating the detector about a reference position for placing the sample. Then, when a tolerance error occurs in the rotation drive axis, it may affect the data to be acquired. For example, if the camera length (sample-to-detector distance) changes due to a tolerance error, the capture angle changes. Even if the same diffraction beam is acquired, since the position where it is detected on the detector plane is changed, angular error occurs.

In the X-ray diffractometer, when a diffraction image is acquired using a reference sample as a powder sample having a known diffraction position, a Debye center (specific position) can be calculated from the observed Debye ring. The deviation amount can be calculated by applying the present invention as the Debye center (u0, v0), it is possible to correct the control or the data of the rotation drive.

Example 1

Figure 9:
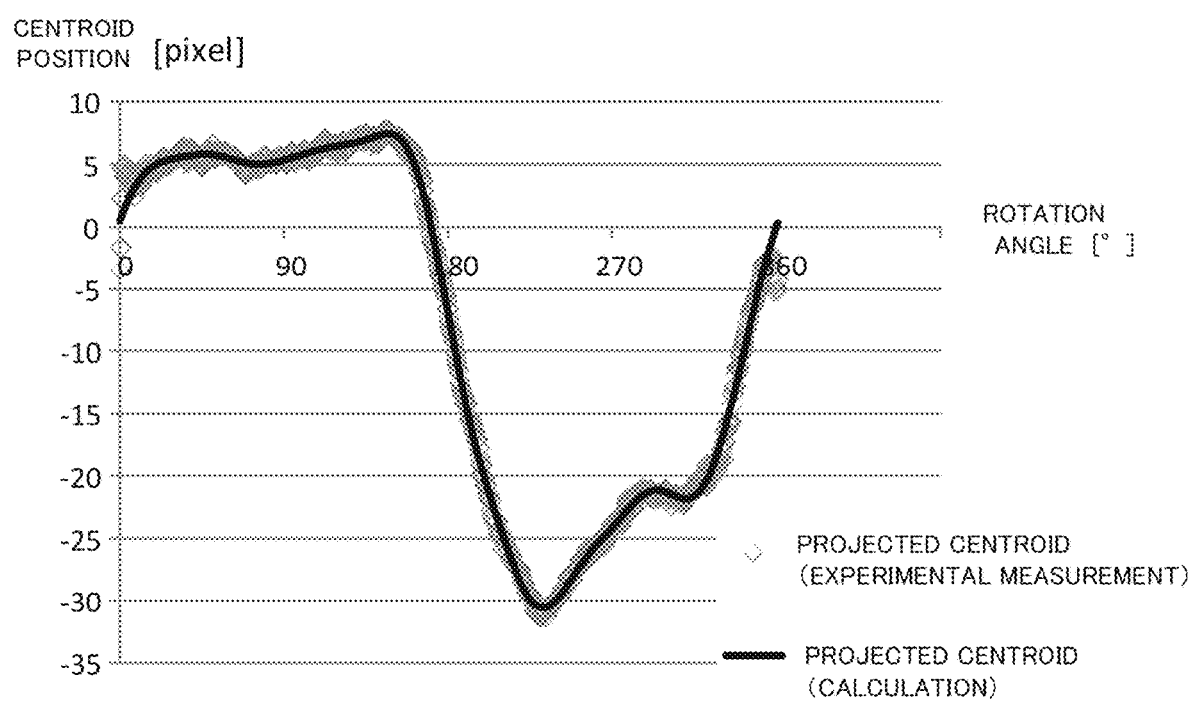
FIG. 9 is a graph showing the centroid position of the projection image of the steel ball in the u direction with respect to the rotation angle.

A steel ball was subjected to CT measurement using an X-ray CT apparatus of gantry rotation type for testing. The centroid position was calculated from the obtained projection image of the steel ball and $\Delta x$ and $\Delta y$ were calculated from the centroid position of the u direction in the experimental measurement. The calculation of $\Delta x$ and $\Delta y$ was optimized using Helgason-Ludwig condition. FIG. 9 is a graph showing the centroid position of the projection image of the steel ball in the u direction with respect to the rotation angle. As shown in FIG. 9, it is confirmed that the measured values coincide with the calculated values for the centroid position in the u direction when the parameters {ai} and {bj} are optimized.

Figure 10:
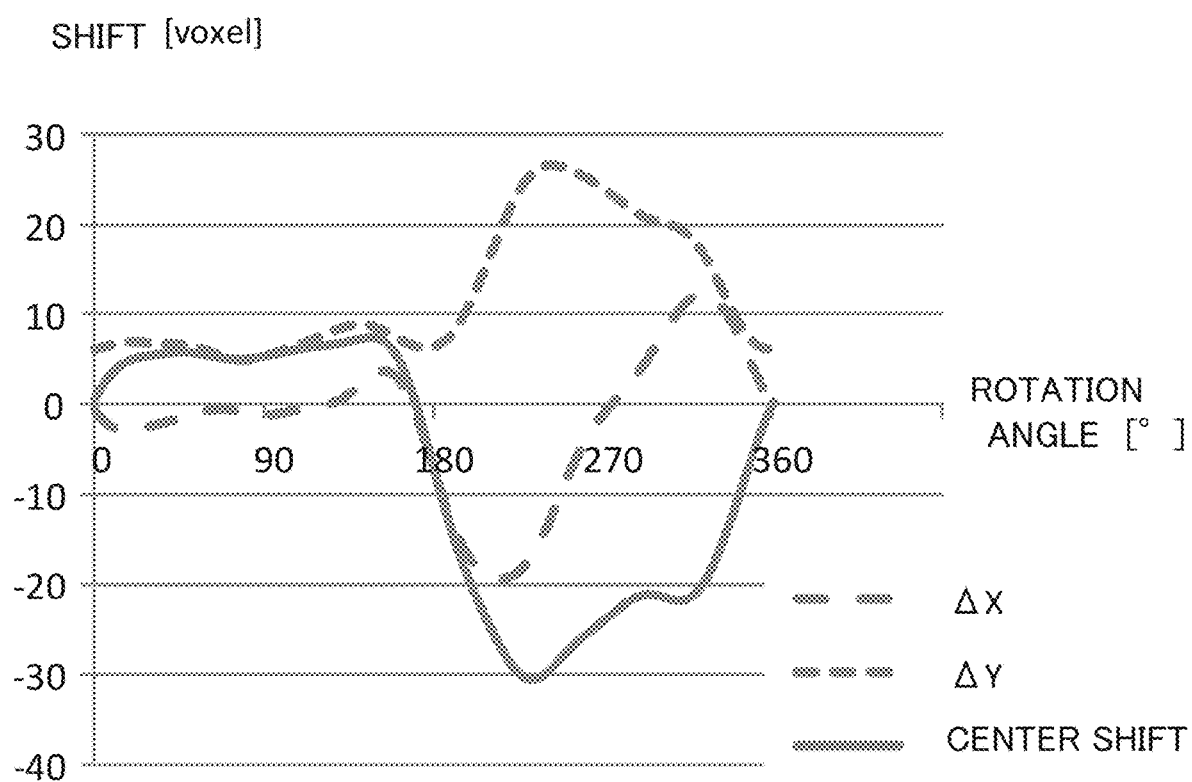
FIG. 10 is a graph showing Δx, Δy and the calculated centroid position in the u direction with respect to the rotation angle.
Figure 11:
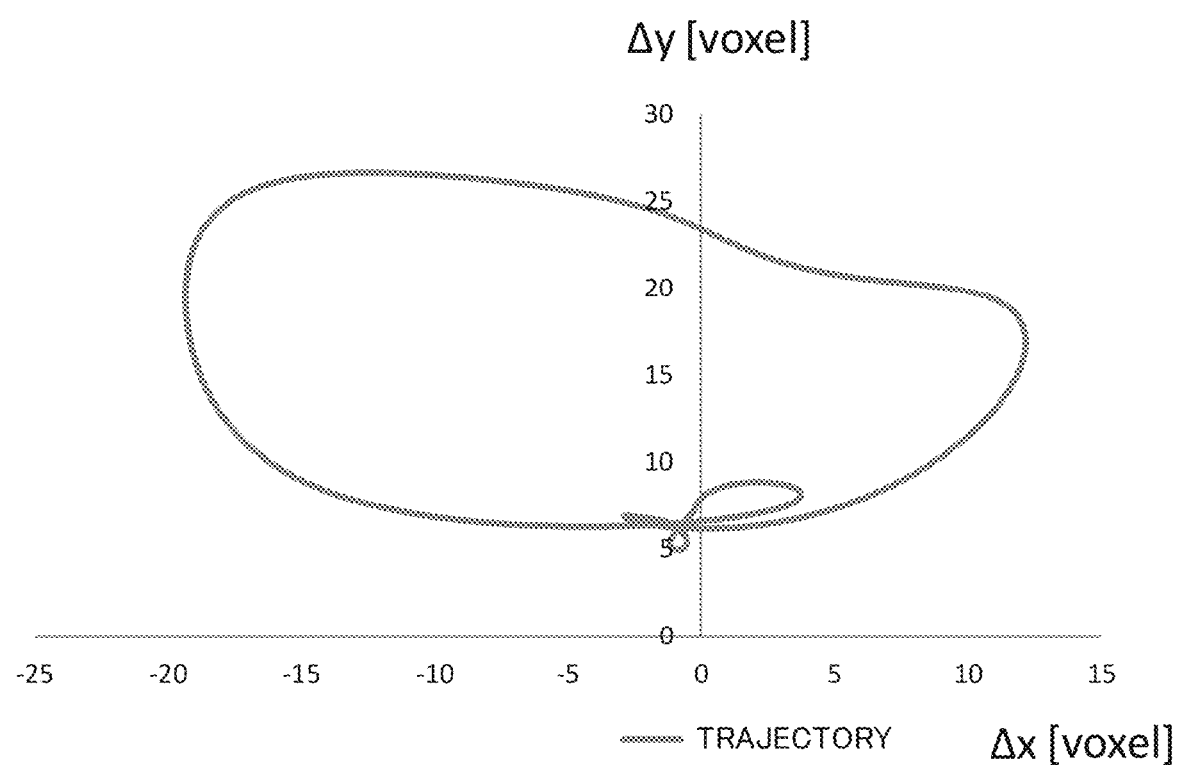
FIG. 11 is a graph showing the trajectory of Δx and Δy over one rotation.
Figure 12:
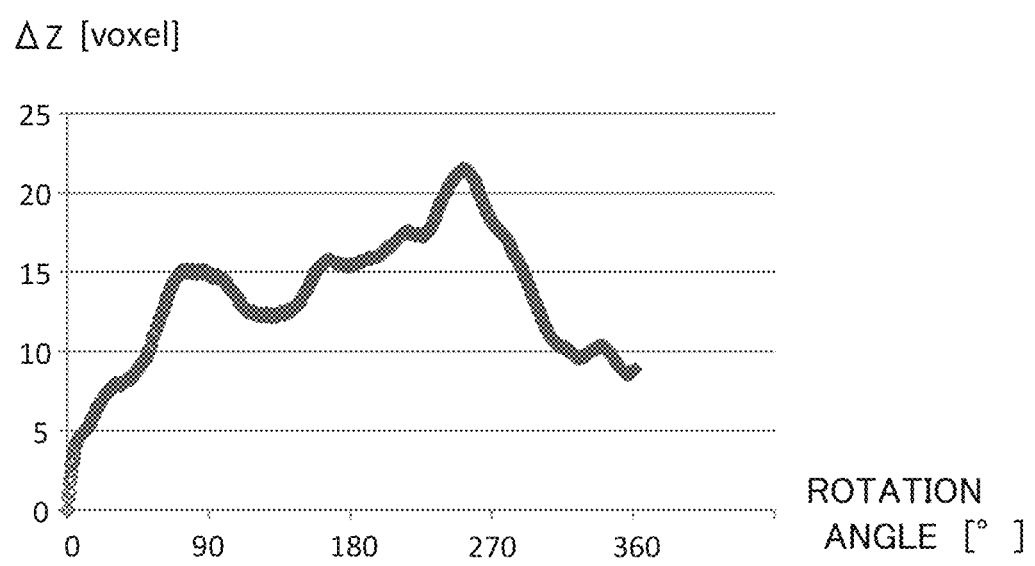
FIG. 12 is a graph showing Δz with respect to the rotation angle.

FIG. 10 is a graph showing $\Delta x$, $\Delta y$ and the calculated centroid position (center shift) in the u-direction with respect to the rotation angle. FIG. 11 is a graph showing the trajectory of $\Delta x$ and $\Delta y$ over one rotation. The deviation amounts of $\Delta x$ and $\Delta y$ of the gantry rotation type X-ray CT apparatus for the test were confirmed. FIG. 12 is a graph showing a deviation $\Delta z$ in the v direction with respect to the rotation angle. By plotting v0 calculated from the CT projection images, the deviation of $\Delta z$ was confirmed.

Figure 13:
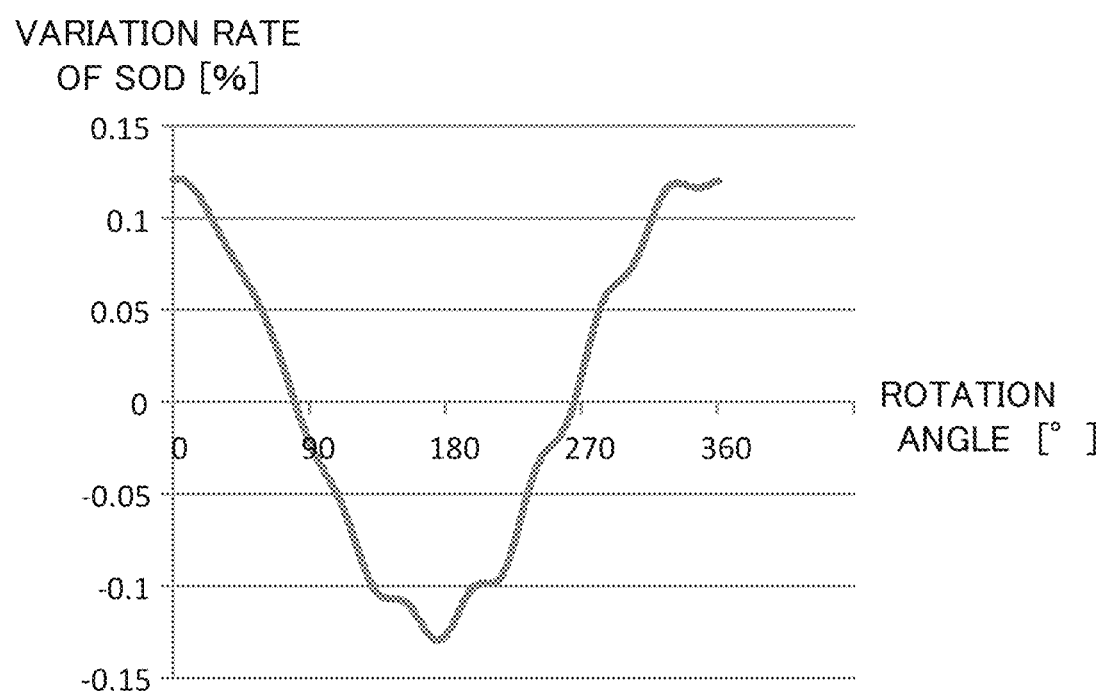
FIG. 13 is a graph showing the variation rate of the SOD with respect to the rotation angle.

SODa(t) was calculated using $\Delta x$ and $\Delta y$ obtained as described above. FIG. 13 is a graph showing the variation rate of SODa(t) with respect to the rotation angle. Thus, the correction amounts used for the correction of the reconstructed image were confirmed.

Example 2

Figure 14A:
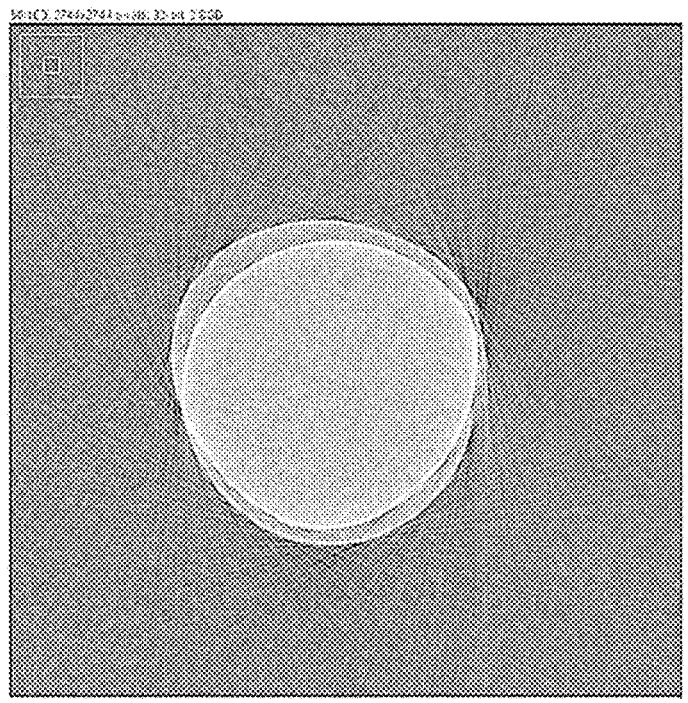
FIGS. 14A and 14B are reconstructed images of steel balls with and without correction, respectively.
Figure 14B:
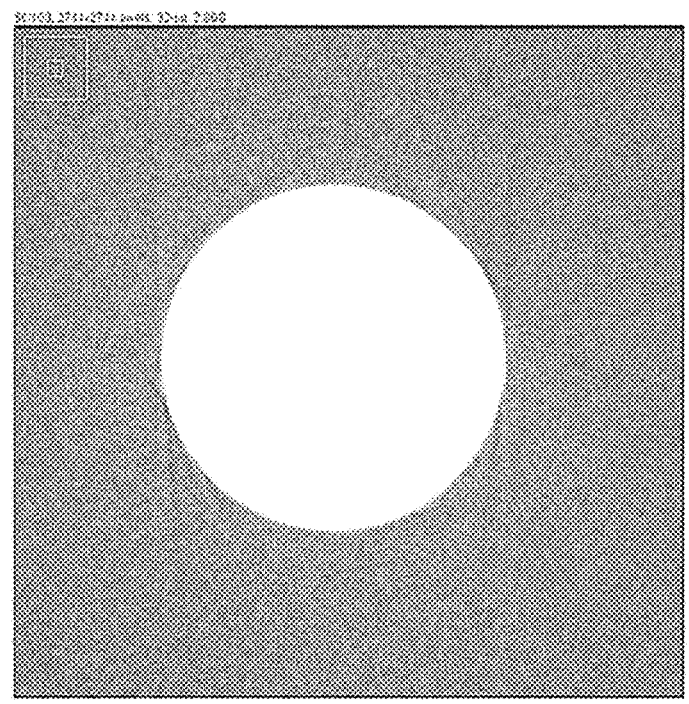

Difference between reconstructed images with and without correction was confirmed. First, the reconstructed image was generated using the projection images without correction for the steel balls used for the calculation of $\Delta x$, $\Delta y$, and $\Delta z$. Next, a reconstructed image was generated using the projection images corrected using the calculated $\Delta x$, $\Delta y$, and $\Delta z$. FIGS. 14A and 14B are reconstructed images of steel balls with and without correction, respectively. It is confirmed that the steel ball is displayed in spherical shapes in FIG. 14A, whereas the steel ball is not displayed in spherical shapes due to blurring in FIG. 14B.

Example 3

Figure 15A:
FIGS. 15A and 15B are reconstructed images of the X-ray test charts with and without correction, respectively.
Figure 15B:
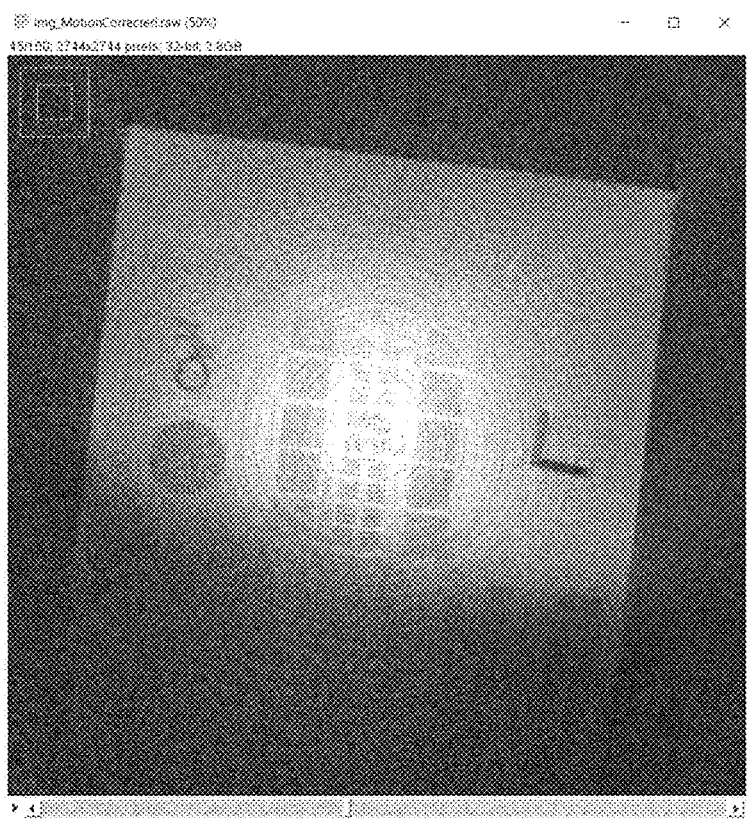

The X-ray test chart was subjected to CT measurement, and first, a reconstructed image was generated using projection images without correction. A reconstructed image was then generated using the projection images corrected using $\Delta x$, $\Delta y$, and $\Delta z$ calculated with a steel ball. FIGS. 15A and 15B are reconstructed images of the X-ray test charts with and without correction, respectively. It is confirmed that the boundary of the pattern of the X-ray test chart is not clear in FIG. 15A, whereas the boundary is clear in FIG. 15B.

In addition, the present application claims priority under the provisions of Paris Treaty Article 4 D (1) based on Japanese Patent Application No. 2021-053075, filed Mar. 26, 2021, and the entire contents of Japanese Patent Application No. 2021-053075 is applied to the present application.

DESCRIPTION OF SYMBOLS 100 system
200 X-ray CT apparatus
210 rotation controlling unit
220 sample position controlling unit
250 sample stage
260 X-ray source
270 detector
300 processing apparatus
310 tolerance error estimating apparatus
311 measurement data storing section
312 device information storing section
320 specific position calculating section
330 deviation calculating section
332 display processing section
335 correction amount calculating section
340 table storing section
345 designation receiving section
350 reconstruction apparatus
360 reconstruction section
370 control apparatus
380 correction controlling section
410 input device
420 display device
L control bus

What is claimed is:

1. A tolerance error estimating apparatus for estimating a tolerance error of a rotation drive axis of an X-ray analysis apparatus, comprising:
a specific position calculating section for obtaining a centroid position of an absorption coefficient as a specific position of a reference sample at each rotation driving time from X-ray detection images acquired by setting the reference sample formed as a sphere of uniform density so that the centroid of the reference sample coincided with the center of a rotation drive shaft, and
a deviation amount calculating section for calculating the deviation amount $\Delta x$ in the x direction and $\Delta y$ in the y direction of the center position of the rotation drive shaft as the rotation drive axis at each rotation driving time from the reference position based on the specific position, when z direction of an orthogonal coordinate system fixed to a sample is set the direction parallel to the rotation drive axis.

2. The tolerance error estimating apparatus according to claim 1,
wherein the amount calculating section assumes respective functional forms of $\Delta x$ and $\Delta y$ for each rotation driving time, determines the function $\Delta x(t)$ used for the calculation of $\Delta x$ and the function $\Delta y(t)$ used for the calculation of $\Delta y$ by optimizing parameters of the assumed functional forms, and uses the determined $\Delta x(t)$ and $\Delta y(t)$ to calculate the $\Delta x$ and $\Delta y$ at each rotation driving time.

3. The tolerance error estimating apparatus according to claim 2,
wherein the deviation amount calculating section optimizes the parameters of the assumed functional form so as to minimize an evaluation function representing a degree of coincidence between the specific position obtained from the X-ray detection images and the specific position calculated using the respective functional forms of the assumed $\Delta x$ and $\Delta y$.

4. The tolerance error estimating apparatus according to claim 2,
wherein the deviation amount calculating section calculates the $\Delta x$ and $\Delta y$ by assuming that the respective functional forms of $\Delta x$ and $\Delta y$ are periodic functions each having a period of rotation drive.

5. The tolerance error estimating apparatus according to claim 1,
wherein the X-ray detection image is acquired by a two-dimensional detector having a detection element with 50 μm or less width.

6. The tolerance error estimating apparatus according to claim 1, further comprising a table storing section storing a table including parameters for correction based on the calculated $\Delta x$ and $\Delta y$.

7. The tolerance error estimating apparatus according to claim 1, further comprising a display processing section for displaying $\Delta x$ and $\Delta y$ over one rotation calculated by the deviation amount calculating section as a trajectory of a tolerance error.

8. The tolerance error estimating apparatus according to claim 1, further comprising a designation accepting section for accepting designation of the means for applying the $\Delta x$ and $\Delta y$,
wherein the tolerance error estimating apparatus activates a reconfiguration function or a control function according to the accepted designation.

9. A reconstruction apparatus, the X-ray analysis apparatus being an X-ray CT apparatus, comprising a reconstruction section for performing reconstruction of a three-dimensional image using the CT projection images obtained by correcting a deviation amount calculated by the tolerance error estimating apparatus according to claim 1.

10. A control apparatus comprising a correction controlling section for controlling correction of the X-ray analysis apparatus based on the deviation amount calculated by the tolerance error estimating apparatus according to claim 1.

11. A tolerance error estimating method for estimating a tolerance error of a rotation drive axis of an X-ray analysis apparatus, comprising steps of:
obtaining a centroid position of an absorption coefficient as a specific position of a reference sample at each rotation driving time from X-ray detection images acquired by setting the reference sample formed as a sphere of uniform density so that the centroid of the reference sample coincided with the center of a rotation drive shaft, and
calculating the deviation amount $\Delta x$ in the x direction and $\Delta y$ in the y direction of the center position of the rotation drive shaft as the rotation drive axis at each rotation driving time from the reference position based on the specific position, when z direction of an orthogonal coordinate system fixed to the sample is set the direction parallel to the rotation drive axis.

12. A non-transitory computer readable recording medium having recorded thereon a tolerance error estimating program for estimating a tolerance error of a rotation drive axis of an X-ray analysis apparatus, the program making a computer execute processes of:
obtaining a centroid position of an absorption coefficient as a specific position of a reference sample at each rotation driving time from X-ray detection images acquired by setting the reference sample formed as a sphere of uniform density so that the centroid of the reference sample coincided with the center of a rotation drive shaft, and
calculating the deviation amount $\Delta x$ in the x direction and $\Delta y$ in the y direction of the center position of the rotation drive shaft as the rotation drive axis at each rotation driving time from the reference position based on the specific position, when z direction of an orthogonal coordinate system fixed to a sample is set the direction parallel to the rotation drive axis.

* * * * *